United States Patent
Katsuda et al.

[11] Patent Number: 5,854,288
[45] Date of Patent: Dec. 29, 1998

[54] USE OF BENZOYLUREAS FOR CONTROLLING HOUSE DUST MITES

[75] Inventors: Yoshio Katsuda, Nishinomiya; Hans-Herbert Schubert, Tokyo, both of Japan; Hilmar Mildenberger, Überlingen, Germany; Stefan Schnatterer, Hattersheim, Germany; Herbert Stark, Kelkheim, Germany

[73] Assignee: Hoechst Schering AgrEvo GmbH, Berlin, Germany

[21] Appl. No.: 646,259

[22] PCT Filed: Nov. 11, 1994

[86] PCT No.: PCT/EP94/03728

§ 371 Date: Aug. 2, 1996

§ 102(e) Date: Aug. 2, 1996

[87] PCT Pub. No.: WO95/13703

PCT Pub. Date: May 26, 1995

[30] Foreign Application Priority Data

Nov. 18, 1993 [JP] Japan .................................. 5-312645
Dec. 11, 1993 [DE] Germany ......................... 43 42 343.4

[51] Int. Cl.⁶ .......................... A01N 43/40; A01N 47/28
[52] U.S. Cl. ........................... 514/594; 514/351; 514/584
[58] Field of Search ................................. 514/351, 594, 514/584

[56] References Cited

U.S. PATENT DOCUMENTS 4,609,676 9/1986 Brouwer et al. ........................ 514/594
4,666,942 5/1987 Anderson ............................... 514/594
4,954,529 9/1990 Koch et al. ............................. 514/594

FOREIGN PATENT DOCUMENTS 0 117 320  5/1984  European Pat. Off. .
WO 90 06680  6/1990  WIPO .

OTHER PUBLICATIONS

A.S. Downing et al. *Chemical Abstracts,* vol. 114, No. 1, Jan. 7, 1991, abstract No. 2243.
A.C. Grosscurt. *Pesticide Science,* vol. 9, 1978, pp. 373–386.
A.C. Grosscurt. *Pesticide Science,* vol. 22, No. 1, 1988, pp. 51–59.

*Primary Examiner*—Allen J. Robinson
*Attorney, Agent, or Firm*—Frommer Lawrence & Haug LLP

[57] ABSTRACT

The use of compounds of the formula I

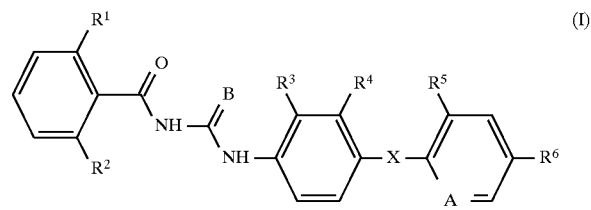

in which $R^1$–$R^6$, A, B und X have the meaning given in detail in the description, for controlling house dust mites. The miticide has a high miticidal effect against house dust mites of Tyrophagus, Dermatophagoides, Cheyletidae, etc. and is harmless to humans and beasts. It is effective not only in exterminating such house dust mites but also in preventing from them.

5 Claims, No Drawings

USE OF BENZOYLUREAS FOR CONTROLLING HOUSE DUST MITES

This application is a 371 of PCT/EP94/03728 filed Nov. 11, 1994.

The invention relates to a method of controlling house dust mites by applying certain benzoylureas as acaricidal active substance.

Numerous kinds of mites live on the earth. For example, mites of *Panonychus citri, Tetranychus urticae*, etc. that are parasitic on plants cause serious damage to crops. Agricultural miticides for mites of these kinds have been developed from the past, and novel and useful compounds have been found one after another in these days.

On the other hand, recent variations in living surroundings result in the increase in mites living in indoor dust (hereinafter referred to as "house dust mites"), such as those of Tyrophagus, Dermatophagoides, Cheyletidae, etc., which are problematic in that they are not only unpleasant but also cause allergic asthma and rash.

In particular large numbers of house dust mites in dwellings are a problem. Their excretions result in dust particles which contain allergenic constituents and can therefore trigger allergic diseases in humans (D. Stollewerk, Allergologie 11 (9), 371–90 (1988)).

The control of house dust mites requires acaricidal active substances which have a high degree of effectiveness, specifically in the relevant species such as *Dermatophagoides farinae, Dermatophagoides pteronyssinus, Euroglyphus maynei, Tyrophagus putrescentiae, Acarus siro, Glycophagus domesticus, lepidoglyphus destructur, Chelacaropsis moorei, Cheyletus eruditus, Cheyletus fortis, Cheletomorpha lepidopterorum* and *Hemicheyletia bakeri,* have a sufficiently good long-term action and can be classified as acceptable with regard to their toxicity to warm-blooded species.

The majority of the commercially available acaricides and insecticides do not have the biological and toxicological properties which are desirable for controlling house dust mites.

It is known that organic phosphorus insecticides such as fenitrothion and diazinon as well as pyrethroid insecticides such as phenothrin and permethrin are effective against such house dust mites living in houses. However, since the miticidal components in these insecticides are all contact poisons, the contact between the insecticides and mites is indispensable. Therefore, when the insecticides are desired to be applied to the place where mites will live, such as the substrate of a carpet, a large amount of it must be applied to its whole surface. However, such is extremely difficult and is not practical, since its safety for human beings, especially infants is not sure. House dust mites are generally weak to heat and will die almost completely at 70° C. for several minutes. In addition, they cannot live under dry conditions. For these reasons, a physical method for treating tatami mats or carpets with high frequency under heat or for drying bedclothes so as to kill mites living therein is effective. However, as being not simple, the method is troublesome. Given the situations, a more suitable method for satisfactorily killing mites is desired.

Benzoylurea compounds are known as inhibitors for the biosynthesis of chitin in insects and mites and have been disclosed in Japanese Patent Laid-Open Application (hereinafter referred to as "JP-A") No. HEI-2-270 to have a high insecticidal and acarical efficacies against various harmful insects such as, for example, mosquitoes, flies and cockroaches as well as mites parasitic on plants.

Benzoylurea compounds such as diflubenzuron and teflubenzuron which have heretofore been developed have high insecticidal and acaricidal activities against sanitary insects such as mosquitoes, flies and cockroaches and mites of Acarina parasitic on plants but are almost ineffective against house dust mites. The reason is considered because of the essential morphological difference between them in that mites of Acarina parasitic on plants belong to the phylum Stigmata while house dust mites belong to the phylum Astigmata.

Furthermore, most insecticidal benzoylphenylureas are well known to be not active against house dust mites.

Surprisingly, it has been found that a group of certain benzoylureas has an outstanding activity against house dust mites.

The invention therefore relates to the use of compounds of the formula I

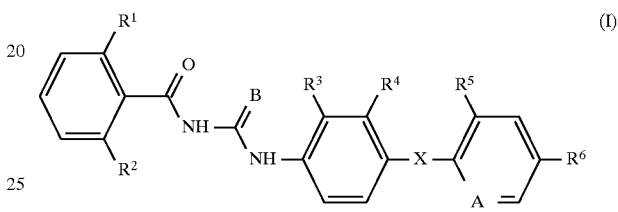

in which
$R^1$ is fluorine or hydrogen,
$R^2$ is fluorine, chlorine or bromine, and
a) $R^3$ is fluorine, hydrogen or methyl,
$R^4$ is fluorine, chlorine or hydrogen,
$R^5$ is fluorine, chlorine, bromine or hydrogen,
$R^6$ is trifluoromethyl,
A is CH or nitrogen,
B is sulfur or oxygen and
X is sulfur or oxygen, or
b) $R^3$, $R^4$ and $R^5$ are in each case hydrogen,
$R^6$ is chlorine, fluorine or hydrogen,
A is CH,
B is oxygen,
X is —$CH_2$—O—N=$CR^7$—, and
$R^7$ is ($C_1$–$C_3$)-alkyl or hydrogen, for controlling house dust mites.

Preferred is the use of compounds of the formula I in which
$R^1$ and $R^2$ are in each case fluorine,
or $R^1$ is hydrogen and $R^2$ is chlorine,
$R^3$ is fluorine or hydrogen,
$R^4$ is chlorine or hydrogen,
$R^5$ is chlorine or bromine,
$R^6$ is trifluoromethyl,
A is CH,
B is oxygen and
X is sulfur or oxygen, and
of compounds of the formula I, in which
$R^1$ and $R^2$ are in each case fluorine
or $R^1$ is hydrogen and $R^2$ is chlorine,
$R^3$, $R^4$ and $R^1$ are in each case hydrogen,
$R^6$ is chlorine,
A is CH,
B is oxygen, X is —CH$_2$—O—N=CR$^7$— and R$^7$ is cyclopropyl.

Particularly preferred is the use of compounds of the formula I, in which

R$^1$ and R$^2$ are in each case fluorine or R$^1$ is hydrogen and R$^2$ is chlorine, R$^3$ is fluorine or hydrogen, R$^4$ is hydrogen, R$^5$ is chlorine, R$^6$ is trifluoromethyl, A is CH, B is oxygen and X is sulfur.

Also particularly useful in the present invention is the use of compound of formula I in which R$^1$ is hydrogen and R$^2$ is chlorine, R$^3$ and R$^4$ are hydrogen, R$^5$ is chlorine, R$^6$ is trifluoromethyl, A is CH B is oxygen and X is sulfur.

The following may be mentioned as examples of compounds of the formula I:

N-(2,6difluorobenzoyl)-N'-[4-(2-chloro-4-trifluoromethylphenylthio)phenyl]urea,

N-(2-chlorobenzoyl)-N'-[4-(2-chloro-4-trifluoromethylphenylthio)phenyl]urea,

N-(2,6-difluorobenzoyl)-N'-[2-fluoro-4-(2-chloro-4-trifluoromethylphenylthio)phenyl]urea, N-(2-chlorobenzoyl)-N'-[2-fluoro-4-(2-chloro-4-trifluoromethylphenylthio)phenyl]urea, N-(2-chlorobenzoyl)-N'-[4-(4-trifluoromethylphenylthio) phenyl]urea, N-(2-chlorobenzoyl)-N'-[3-chloro-4-(2-chloro-4-trifluoromethylphenylthio)phenyl]urea, N-(2,6-difluorobenzoyl)-N'-[2-fluoro-4-(2-chloro-4-trifluoromethylphenoxy)phenyl]urea, N-(2-chlorobenzoyl)-N'-[2-fluoro-4-(2-chloro-4-trifluoromethylphenoxy)phenyl]urea, N-(2,6-difluorobenzoyl)-N'-[4-(α-cyclopropyl-4-chloro-benzylideneaminoxymethyl)phenyl]urea and N-(2,6-chlorobenzoyl)-N'-[4(α-cyclopropyl4-chlorobenzylideneaminoxymethyl)phenyl]-urea.

Benzoylureas of the formula I and processes for their preparation are disclosed, for example, in EP-A-318882, EP-A-161019, JP-A-63156765 and EP-A-117320.

Where a Benzoylurea of the formula I is employed as an active ingredient in a miticide for house dust mites according to the present invention, it may be used directly as it is, without adding any other component thereto, but, in general, it is mixed with solid carriers, liquid carriers, gaseous carriers, surfactants, other auxiliary additives for insecticidal preparations, feed, etc. and formulated and shaped into powder, granules, aerosol, emulsion, aqueous solution, fumigants, poisoned bait, sheet, etc.

Consequently, the invention also relates to compositions for use in the control of house dust mites which contain the compounds of the formula I in addition to suitable formulation auxiliaries. In general, the compositions according to the invention contain 0.1 to 98% by weight, preferably 0.5 to 95% by weight, of active substance of the formula I. They can be formulated in various ways, depending on the specific requirements and the prevailing biological and/or chemico-physical parameters. The following are therefore suitable possibilities for formulation: wettable powder (WP), emulsifiable concentrates (EC), aqueous solutions (SC), emulsions, sprayable solutions, oil- or water-based dispersions (SC), suspoemulsions (SC), dusts (DP), seed-dressing products, granules in the form of microgranules, spray granules, coated granules, and adsorption granules, water-dispersible granules (WG), ULV formulations, microcapsules, waxes or baits.

These individual types of formulation are known in principle and are described, for example, in:

Winnacker-Küchler, "Chemische Technologie" [Chemical Technology], Volume 7, C. Hauser Verlag Munich, 4th Ed. 1986; van Valkenburg, "Pesticide Formulations", Marcel Dekker N.Y., 2nd Ed. 1972–73; K. Martens, "Spray Drying Handbook", 3rd Ed. 1979, G. Goodwin Ltd. London. Individual formulations are also disclosed in the above-mentioned disclosures.

The formulation auxiliaries required, such as inert materials, surfactants, solvents and other additives, are also known and are described, for example, in: Watkins, "Handbook of Insecticide Dust Diluents and Carriers", 2nd Ed., Darland Books, Caldwell N.J.; H. V. Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's "Detergents and Emulsifiers Annual", MC Publ. Corp., Ridgewood N.J.; Sisley and Wood, "Encyclopedia of Surface Acitve Agents", Chem. Publ. Co. Inc., N.Y. 1964; Schönfeldt, "Grenzflächenaktive Äthylenoxidaddukte" [Surface-active Ethylene Oxide Adducts], Wiss. Verlagsgesellschaft, Stuttgart 1976; Winnacker-Küchler, "Chemische Technologie" [Chemical Technoloy], Volume 7, C. Hauser Verlag Munich, 4th Ed. 1986.

As surfactants, any available substances may be employed, including, for example, salts of alkysulfate esters, salts of alkylsulfonic acids, polyoxyethylene alkyl ethers, sorbitan fatty acid esters, polyoxyethylene-polyoxypropylene block copolymers, etc. As auxiliary additives for insecticidal preparations, suitable are dispersing agents, sticking agents, stabilizers, etc.

Wettable powders are preparations which are uniformly dispersible in water and which, besides the active substance, also comprise wetting agents, for example polyoxyethylated alkylphenols, polyoxyethylated fatty alcohols, alkyl- or alkylphenolsulfonates and dispersants, for example sodium lignosulfonate, sodium 2,2'-dinaphtylmethane-6,6'-disulfonate, sodium dibutyl-naphtalenesulfonate or else sodium oleylmethyltauride, in addition to a diluent or inert substance.

Emulsifiable concentrates are prepared by dissolving the active substance in an organic solvent, for example butanol, cyclohexanone, dimethylformamide, xylene, or else higher-boiling aromatics or hydrocarbons, with the addition of one or more emulsifiers. Examples of emulsifiers which can be used are: calcium alkyaryl sulfonates, such as calcium dodecylbenzenesulfonate, or non-ionic emulsifiers, such as fatty acid polyglycol ester, alkylaryl polyglycol ethers, fatty alcohol polyglycol ethers, propylene oxide/ethylene oxide condensation products, alkyl polyethers, sorbitan fatty acid ester, polyoxyethylene sorbitan fatty acid ester, or polyoxyethylene sorbitol esters.

Dusts are obtained by grinding the active substance with finely divided solid substances, for example talc, natural clays such as kaolin, bentonite, pyrophyllite, or diatomaceous earth. Granules can be prepared either by atomizing the active substance onto adsorptive, granulated inert material, or by applying active substance concentrates onto the surface of carrier materials, such as sand, kaolinites or granulated inert material, by means of adhesives, for example polyvinyl alcohol, sodium polyacrylate or else mineral oils.

Based on these formulation, it is also possible to prepare combinations with other pesticidally active substances, for example in the form of a readymix or a tank mix. Inter alia to the miticide for house dust mites of the present invention, may be added other miticides, insecticides, microbicides, repellents, synergists, antiseptics, growth inhibitors, aromatics, colorants, etc. so as to prepare multipurpose compositions, provided that such additives do not retard the activity of Compound of formula I in the resulting compositions. For instance, as insecticides, mentioned are organic phosphorus insecticides such as fenitrothion, diazinon, propetamphos, etc.; pyrethroid insecticides such as phenothrin, permethrin, resmethrin, etofenprox, empenthrin, etc.; and other compounds such as silafluofen, diflubenzuron, teflubenzuron, chlorfluazuron, fluphenoxron, pyriproxyfen, etc. As repellents, mentioned are N,N-diethyl-m-toluamide, benzyl benzoate, etc. As synergists, mentioned are piperonyl butoxide, octachlorodipropyl ether, N-(2-ethylhexyl)-bicyclo[2.2.1]hept-5-ene-2,3-dicarboximide, isobornyl thiocyanoacetate, etc.

The concentration of active substance in wettable powders is, for example, approximately 10 to 90% by weight, the remainder to 100% by weight being composed of customary formulation components. In the case of emulsifiable concentrates, the active substance concentrations can be approximately 5 to 80% by weight. Formulations in the form of dusts usually contain 5 to 20% by weight of active substance, sprayable solutions approximately 2 to 20% by weight. In the case of granules, the active substance content depends partly on whether the active compound is in dissolved or solid form, and on which granulation auxiliaries, fillers etc. are used.

In addition, the active substance formulations mentioned contain, if appropriate, the binders, wetting agents, dispersants, emulsifiers, penetrants, solvents, fillers or carriers which are customary in each case.

Suitable solid carriers include, for example, clays (e.g. kaolin, bentonite, etc.), talcs, silicas, alumina powder, active charcoals, vegetable powders, etc. Suitable liquid carriers are solvents, including, for example, water, alcohols (e.g. methyl alcohol, ethyl alcohol, ethylene glycol, etc.), ketons (e.g., acetone, methyl ethyl ketone, cyclohexanone, etc.), ethers (e.g., ethyl ether, dioxane, cellosolves, etc.), aliphatic hydrocarbons (e.g., gasoline, kerosene, lamp oil, etc.), aromatic hydrocarbons (e.g., benzene, toluene, xylene, methylnaphtalene, etc.), halogenated hydrocarbons (e.g., dichloromethane, trichlorobenzene, etc.), esters, acid amides, nitrites, etc. These may be employed singly or as mixtures of two or more of them. As gaseous carriers, usable are LPG (liquefied petroleum gas), dimethyl ether, freon gas, etc.

For use, the concentrates, which are in commercially available form, are, if appropriate, diluted in the customary manner, for example using water in the case of wettable powders, emulsifiable concentrates, dispersions and, in some cases, also microgranules. Preparations in the form of dusts and granulated preparations as well as sprayable solutions are conventionally not diluted any further with other inert substances prior to use.

The application rate rquired varies with the external conditions such as, inter alia, temperature and humidity. It can vary within wide limits in the case of surface treatment, for example, between 1 and 500 mg/m$^2$ or more of active ingredient.

The active substances according to the invention can be present both in their commercially available formulations and in the use forms prepared form these formulations in mixtures with other biologically active substances.

The active substance content of the use forms, prepared from the commercially available formulations, can vary in wide ranges and the amount of the active ingredient to be in the miticide for house dust mites of the present invention and the amount of the miticide to be used may be determined suitably, depending on the form of the miticide, the object which shall be exterminated by the miticide, the method how to use the miticide and the place to which the miticide is applied etc. Application is effected in a customary manner adapted to suit one of the use forms. To control the house dust mites, the formulations of the compounds of the formula I are applied to the surfaces, materials and objects to be treated (such as textiles, wall paper, floor coverings, cushion stuffings) which are infested with dust mites. Textiles can, for example, also be washed or soaked in liquors containing active substances.

For instance, in order to exterminate mites of Dermatophagoides which live in carpets, it is preferred that Compound of formula I is applied to them in an amount of 0.1 mg/m$^2$ or more. Since Compound of formula I acts not only as a contact poison but also as a stomach poison, a poisoned bait composition to be prepared by adding Compound of formula I to feed, etc. is a preferred embodiment for using the compound. The composition may display a sufficient effect, when containing from 0.1 ppm to 1.0% of the active compound.

The invention also relates to the prophylactic treatment (such as impregnation or coating) of surfaces, materials and objects with compounds of the formula I or formulations thereof against infestation with dust mites.

As acting both as a contact poison and as a stomach poison, Compound of formula I may characteristically display a high miticidal effect even when it is partly, but not uniformly and completely, applied to the place where mites, if any, shall be exterminated by it. As opposed to this, the conventional organic phosphorus miticides and pyrethroid miticides act only as contact poisons and repel more or less house dust mites, so that they cannot display their miticidal effect when applied partly. As mentioned above, the miticide for house dust mites of the present invention has a high miticidal effect against house dust mites such as those of Tyrophagus, Dermatophagoides, Cheyletidae, etc., while being extremely safe for humans and beasts. Therefore, the present invention provides a more advantageous method for exterminating house dust mites by the use of the chemical compound than the conventional method using known organic phosphorus miticides or pyrethroid miticides. Since Compound of formula I is chemically stable and is slowly released from the composition containing it, the miticide of the present invention is extremely useful not only for exterminating house dust mites that have already grown but also as a so-called preventive composition to be applied to carpets, bedclothes, etc. for protecting them from being infected by mites.

The examples which follow are intended to illustrate the invention without imposing any limitation thereto.

A. Formulation examples
  a) A dust is obtained by mixing 10 parts by weight of active substance and 90 parts by weight of talc as inert substance and comminuting the mixture in a hammer mill.
  b) A wettable powder which is readily dispersible in water is obtained by mixing 25 parts by weight of active substance, 65 parts by weight of kaolin-containing quartz as inert substance, 10 parts by weight of potassium lignosulfonate and 1 part by weight of sodium oleylmethyltauride as wetting agent and dispersant and grinding the mixture in a pinned-disk mill.

c) A dispersion concentrate which is readily dispersible in water is prepared by mixing 40 parts by weight of active substance with 7 parts by weight of a sulfosuccinic monoester, 2 parts by weight of a sodium lignosulfonate and 51 parts by weight of water and grinding the mixture in a ball mill to a fineness of below 5 microns.

d) An emulsifiable concentrate can be prepared from 15 parts by weight of active substance, 75 parts by weight of cyclohexanone as solvent and 10 parts by weight of oxethylated nonylphenol (10 EO) as emulsifier.

e) Granules can be prepared from 2 to 15 parts by weight of active substance and an inert granule carrier material such as attapulgite, pumice granules and/or quartz sand. It is expedient to use a suspension of the wettable powder of Example b) with a solids content of 30%, which is sprayed onto the surface of attapulgite granules, and these are dried and mixed intimately. The content by weight of the wettable powder is approximately 5% and of the inert carrier material approximately 95% of the finished granules.

TABLE 1

Compounds of the formula I ($R^6 = CF_3$)

| Compound No. | $R^1$ | $R^2$ | $R^3$ | $R^4$ | $R^5$ | X | A | B |
|---|---|---|---|---|---|---|---|---|
| 1 | H | Cl | H | H | Cl | S | CH | O |
| 2 | F | F | H | H | Cl | S | CH | O |
| 3 | H | Cl | F | H | Cl | S | CH | O |
| 4 | F | F | F | H | Cl | S | CH | O |
| 5 | H | Cl | H | H | Cl | S | CH | S |
| 6 | F | F | H | H | Cl | S | CH | S |
| 7 | H | Cl | H | Cl | Cl | S | CH | O |
| 8 | F | F | H | Cl | Cl | S | CH | O |
| 9 | H | Cl | H | H | H | S | CH | O |
| 10 | F | F | H | H | H | S | CH | O |
| 11 | H | Cl | F | H | Cl | O | CH | O |
| 12 | F | F | F | H | Cl | O | CH | O |
| 13 | H | Cl | H | H | Cl | S | N | O |
| 14 | F | F | H | H | Cl | S | N | O |

TABLE 2

Compounds of the formula I ($R^3$, $R^4$, $R^5$ = H; A = CH, B = O, X = —$CH_2$—O—N = $CR^7$—)

| Compound No. | $R^1$ | $R^2$ | $R^7$ | $R^6$ |
|---|---|---|---|---|
| 15 | F | F | Cyclopropyl | Cl |
| 16 | H | Cl | Cyclopropyl | Cl |
| 17 | F | F | $C_2H_5$ | Cl |
| 18 | H | Cl | $C_2H_5$ | Cl |

B. Biological examples

The compounds of the formula I are tested on house dust mites of the species *Dermatophagoides pteronyssinus* (D.p.) and *Tyrophagus putrescentiae* (T.p.).

The efficacy was determined when the active substance was administered orally (feed mix method).

The following commercially availabe insect growth inhibitors, as well as benzoylureas (A, B), juvenoids (C, D) and pyrethroid (E) were used as comparison substances:

A diflubenzuron, wettable powder (W.P.)

B teflubenzuron (5% E.C.)

C pyriproxifen (0.5% G.)

D methoprene (10%)

E phenotrin

The tests showed that low concentrations of the compounds of the formula I allowed complete control of the dust mites to be achieved, while the comparison substances show no, or only low levels of, activity.

Experiment 1

Test method: Feed mix method

Each test compound is intimately mixed with pulverulent animal feed, and a mixture is prepared which is twice as strong as the test concentration. This preparation of active substance is mixed with the same animal feed which contains a defined quantity of the abovementioned harmful organisms (approximately 450 mites/gram in the case of D.p. and approximately 100 mites/gram in the case of T.p.) in a ratio of 1:1, resulting in the desired test concentration.

A control feed without active substance is prepared analogously.

5 g portions of each mixture are stored in a Petri dish having a diameter of 4.5 cm and a height of 1.5 cm. The dishes having therein mites of *Dermatophagoides pteronyssinus* were put in a container having a conditioned reative humidity of about 65%, while those having therein mites of *Tyrophagus putrescentiae* were in a container having a conditioned relative humidity of about 85%. These containers were set in a thermostatic room having a temperature of 25°±1° C., where the mites were cultivated.

On one, two and three weeks or merely on two and three weeks after the treatment, respectively, each medium was lightly stirred so as to uniformly disperse the mites growing therein. Then, 0.1 g of each medium was sampled, and the number of the mites living therein was counted using a stereoscopic microscope. The sampling to count the number of the living mites was effected three times for each test group, and the average of the counted data was obtained. From the thus-obtained mean value, the percentages of growth inhibition on one, two and three weeks or on two and three weeks, resp., were calculated according to the following equation.

$$\text{Control rate } [\%] = \frac{C - T}{C} \times 100$$

C: Number of live mites in the control mixture

T: Number of live mites in the mixtures containing active substance

The results obtained are shown in Table 3.

TABLE 3

| Tested compound and concentration [ppm] | | Control rate of dust mites [%] | | | | | |
|---|---|---|---|---|---|---|---|
| | | D. pteronyssinus | | | T. putrescentiae | | |
| | | 1 week | 2 weeks | 3 weeks | 1 week | 2 weeks | 3 weeks |
| Compound 1 | 0.4 | — | 50 | 80 | — | 100 | 100 |
| | 2 | — | 92 | 98 | — | 100 | 100 |
| | 10 | 59.1 | 94.8 | 96.9 | 89.6 | 99.7 | 100 |
| | 50 | 69.3 | 94.5 | 98.2 | 83.4 | 98.8 | 99.8 |
| | 100 | — | 100 | 100 | — | 100 | 100 |
| | 250 | 76.9 | 96.7 | 98.0 | 98.2 | 100 | 100 |
| Diflubenzuron W.P. | 100 | — | 0 | 0 | — | 17 | 3 |
| | 250 | 1.2 | 0 | 0 | 0 | 17.4 | 3.2 |
| | 2500 | 7.7 | 6.2 | 0 | 0 | 49.2 | 31.7 |
| Pyriproxifen | 100 | — | 0 | 0 | — | 15 | 10 |
| | 250 | 21.4 | 0 | 0 | 0 | 26.3 | 18.2 |
| | 2500 | 28.3 | 0 | 0 | 0 | 30.1 | 28.4 |
| Methoprene | 10 | 0 | 28.2 | 6.8 | 20.8 | 36.4 | 29.0 |
| | 100 | — | 20 | 15 | — | 32 | 30 |
| | 250 | 22.1 | 15.8 | 23.6 | 29.2 | 31.6 | 37.2 |
| | 2500 | 16.8 | 34.2 | 30.6 | 20.8 | 19.7 | 14.3 |
| Phenothrin | 10 | — | 65 | 60 | — | 20 | 20 |
| | 100 | — | 97 | 99 | — | 88 | 90 |
| Teflubenzuron | 10 | 4.0 | 18.5 | 0 | 0 | 33.0 | 0 |
| | 100 | — | 50 | 46 | — | 40 | 20 |
| | 250 | 57.4 | 92.4 | 98.8 | 50.0 | 65.0 | 59.7 |
| | 2500 | 100 | 100 | 100 | 100 | 100 | 100 |
| Development of the mite population in the control mix: | | | | | | | |
| Population density (mites/0.1 g) | | 82.3 | 291 | 886 | 21.7 | 231 | 1205 |
| | | 43.3 | 273 | 613 | 16.3 | 264 | 1863 |
| | | 101 | 298 | 1.036 | 25.3 | 185 | 743 |
| | | | | | 24.0 | 294 | 1354 |

The feed mix trial shows that compound 1 in a concentration range of 10 ppm effects a complete control of house dust mites when the active substance is taken up orally. In the same concentration range, the comparison substances achieve a control success of only 0–33%. Compound of formula I it was highly effective against *Dermatophagoides pteronyssinus* and *Tyrrophagus putrescentiae,* showing extremely high percentages of growth inhibition, even though its concentration was low. As opposed to this, the other benzoylurea compounds such as diflubenzuron and teflubenzuron and juvenile hormones such as methoprene and pyroproxifen that were used as control chemicals did not almost have the growth inhibiting effect. From this, it has been clarified that the miticidal activity against house dust mites is peculiar to compound of formula I chosen from among benzoylurea compounds. On the other hand, phenothrin which belongs to pyrethroid compounds and is essentially used as the active integrdient in conventional miticides for house dust mites required a high concentration so as to display its miticidal activity. Accordingly, compound of formula I which is almost harmless to humans and beasts and shows an extremely high miticidal activity at a low concentration may be an extremely advantageous active ingredient in an miticide for house dust mites, in place of conventional active ingredients such as phenothrin, etc.

Experiment 2

Test method: Carpet impregnation

Each test compound is sprayed onto square pieces of carpet (5×5 cm, 100% wool, pile length 7 mm) in the form of a solution in acetone, treatment amounts of 20 and 100 mg/m$^2$ being applied.

The untreated pieces of carpet (control) are sprayed with pure acetone without dissolved chemicals and dried. These were dried in the atmosphere for 3 hours. 0.5 g of a medium having therein about 450 mites of *Dermatophagoides pteronyssinus* were planted on each carpet piece, put in a container having a conditioned relative humidity of about 65% and set in a thermostatic room having a temperature of 25°±1° C. After one week intervals, pieces of carpet are taken, and the number of live mites is determined. Heating the carpet pieces with a hot plate, the mites living in each piece were driven out whereupon the number of the living mites was counted. The same test was repeated three times for each group, and the average value was obtained from the measured data. From the number of the living mites in the chemical-treated group and that in the control group, the percentage of growth inhibition was calculated according to the following equation. The carpet treated with the test chemical and stored for one month at 40° C. was also tested in the same manner as above.

$$\text{Control rate } [\%] = \frac{C - T}{C} \times 100$$

C: Number of live mites in the control mixture
T: Number of live mites in the mixtures containing active substance The results are shown in Table 4.

TABLE 4

Number of live mites in the carpet, and control rate

| | Time after application [weeks] | | | | |
|---|---|---|---|---|---|
| | Immediately after treatment of carpet | | | Stored for one month at 40° C. after treatment of carpet pieces | |
| Test compound and dosage [mg/m²] | 1 | 2 | 4 | 2 | 4 |
| Compound 1 | 198 | 76 | 57 | — | — |
| 20 | 59.8% | 96.4% | 99.3% | 94% | 100% |
| 100 | 167 | 85 | 52 | — | — |
| | 66.1% | 96.0% | 99.4% | 96% | 100% |
| Diflubenzuron | — | — | — | — | — |
| 100 | — | 0% | 0% | 0% | 0% |
| Teflubenzuron | — | — | — | — | — |
| 100 | — | 20% | 15% | 10% | 5% |
| Control | 493 | 2130 | 8763 | | |

The carpet impregnation trial shows that the effectiveness of the benzoylureas of the formula I against dust mites commences after one week and continues, showing an excellent long-term action.

Particularly, the test results verified that compound of formula I also had an extremely high percentage of growth inhibition when used for so-called preventive treatment of carpets at a low concentration. In addition, compound of formula I has also been proven by these results to have excellent long residual activity. Accordingly, the compound is extremely useful as an anti-mite agent for house dust mites living in carpets, bedclothes, etc. As opposed to this, the other benzoylurea compounds such as diflubenzuron and teflubenzuron were ineffective.

Experiment 3

Pieces each having a size of 5 cm×5 cm that were prepared from the same carpet as that employed in Experiment 2. The periphery of one cm wide of each carpet piece was treated with a test chemical (see Table 5 below), while its center was not. The amount of the chemical indicated in Table 5 below was per m² of the whole surface of each test piece. 0.2 g of a medium containing therein about 200 mites of *Dermatophagoides pteronyssinus* were planted on the center of the test piece to which no chemical had been applied. Each carpet piece was put in a container having a conditioned relative humidity of 65% and set in a thermostatic room having a temperature of 25°±1° C.

The percentage of growth inhibition was obtained for each test piece in the same manner as in Experiment 2, and the results are shown in Table 5.

The test results verified the high miticidal effect of compound of formula I which had been partly applied to carpet pieces while mites of *Dermatophagoides pteronyssinus* had been planted in the area of each carpet piece to which the compound had not been applied. From the fact, it is considered that compound of formula I did not repel the mites but acted on them not only as a contact poison but also as a stomach poison whereby the mites were exterminated due to such characteristics of compound for formula I. As opposed to this, hoewever, the pyrethroid compound phenothrin displayed its miticidal effect to some degree only when it was applied to the whole surface of each carpet piece at the concentration designated in Table 5 above, while it was almost ineffective when partly applied thereto. From the fact, it is presumed that the contact between phenothrin and mites will be inhibited due to the repelling activity of phenothrin so that phenothrin could not act on mites as a contact poison.

In practical use, it is often impossible to apply a miticide to the whole surface of an object where mites, if any, shall be exterminated by the miticide. Considering the practical situation, compound of formula I which is effective even when it is partly applied to objects is extremely advantageous in its practical use.

Emperiment 4

0.7 g of compound 1 were dissolved in ethanol and filled in an empty aerosol container, to which was fitted a valve part. Through the valve part, a propellant was charged into the container under pressure to complete an aerosol container filled with compound 1 (300 ml). The aerosol were

TABLE 5

| | | Chemical Tested | Amount of Active Ingredient (mg/m²) | Percentage of Growth Inhibition (%) | |
|---|---|---|---|---|---|
| | | | | after 2 weeks | after 4 weeks |
| Samples of the Invention | 1 | Compound 1 | 20 | 50 | 100 |
| | 2 | Compound 1 | 100 | 90 | 100 |
| Control Samples | 1 | phenothrin | 100 | 5 | 0 |
| | 2 | phenothrin (whole surface treated uniformly) | 100 | 60 | 50 | sprayed over a two-mat carpet (ca. 3.2 m²) in an amount of 30 ml (20 mg/m² as the active ingredient). After one month, about 500 mites of *Dermatophagoides farinae* were inoculated into the carpet. Meanwhile, the propagation of the mites was inhibited and the density of the living mites was reduced to 5% or less of the original one. The result verified the high miticidal effect of compound of formula I capable of preventing the growth of mites.

Experiment 5

0.1 g of compound 1, 0.2 g of N-(2-ethylhexyl)-bicyclo-[2.2. 1]hept-5-ene-2,3-dicarboximide and 99.7 g of powdery feed were well ground and mixed to prepare a poisoned bait composition. This was sprayed over a carpet having a size of 10 cm×10 cm, which had been inoculated with about 300 mites of *Dermatophagoides pteronyssinus* and about 200 mites of Cheyletidae, in an amount of 20 g per m² (20 mg/m² as the active ingredient). After 2 weeks, the number of the living mites was counted to be 10 mites or less each.

We claim:

1. A method for controlling infestation of house dust mites which comprises applying to said dust mites or to an infested locus where they reside an effective amount of a compound selected from the group consisting of

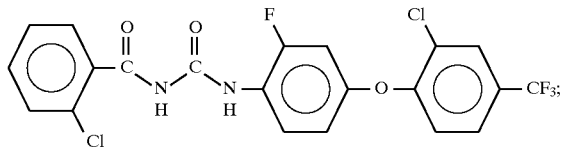

and

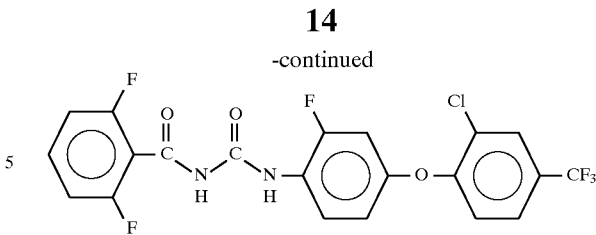

2. The method according to claim 1, wherein the compound is

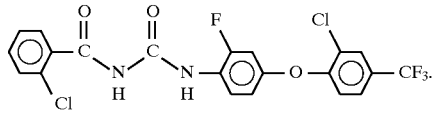

3. The method according to claim 1, wherein the compound is

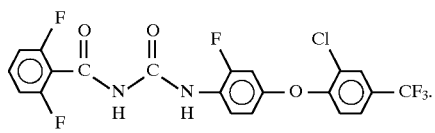

4. The method according to claim 1, wherein the house dust mite is *Dermatophogoides farniae; Dermatophogoides pteronyssinus; Eurolyphus maynei; Trophagus putrescentiae; Glycophagus demesticus, Lepidoglyphus destructur; Chelacaropsis moorei; Cheyletus eruditus, Cheylitus fortis; Cheletomorpha lepidopterorum* and *Hemicheyletia bakeri.*

5. The method according to claim 1, wherein the is *Dermatophoaoides farniae.*

* * * * *